(12) United States Patent
Smits

(10) Patent No.: US 6,887,213 B2
(45) Date of Patent: May 3, 2005

(54) ANKLE-FOOT ORTHOSIS

(75) Inventor: Jan F. A. Smits, Helmond (NL)

(73) Assignee: Camp Scandinavia AB, Helsingborg (SE)

( * ) Notice: Subject to any disclaimer, the term of this patent is extended or adjusted under 35 U.S.C. 154(b) by 0 days.

(21) Appl. No.: 10/473,278

(22) PCT Filed: Apr. 18, 2002

(86) PCT No.: PCT/SE02/00765
§ 371 (c)(1),
(2), (4) Date: Sep. 30, 2003

(87) PCT Pub. No.: WO02/083040
PCT Pub. Date: Oct. 24, 2002

(65) Prior Publication Data
US 2004/0102727 A1 May 27, 2004

(30) Foreign Application Priority Data
Apr. 18, 2001 (SE) .................................. 0101341

(51) Int. Cl.$^7$ .................................................. A61F 5/00
(52) U.S. Cl. .......................................... 602/27; 602/23
(58) Field of Search ............................ 602/28, 19, 23, 602/29, 30, 60, 61, 62; 623/27, 28, 47

(56) References Cited

U.S. PATENT DOCUMENTS

| | | | | |
|---|---|---|---|---|
| 2,847,991 A | * | 8/1958 | Andrews ...................... 602/28 |
| 2,949,111 A | * | 8/1960 | Ruotoistenmaki ............ 602/28 |
| RE33,762 E | * | 12/1991 | Lonardo ....................... 602/27 |
| 5,219,324 A | * | 6/1993 | Hall .............................. 602/28 |
| 5,817,041 A | * | 10/1998 | Bader ........................... 602/23 |
| 5,897,515 A | * | 4/1999 | Willner et al. ................ 602/27 |
| 6,146,344 A | * | 11/2000 | Bader ............................. 602/6 |
| 6,676,618 B2 | * | 1/2004 | Andersen ....................... 602/7 |

FOREIGN PATENT DOCUMENTS

DE 19722118 2/1999

* cited by examiner

Primary Examiner—Henry Bennett
Assistant Examiner—Shumaya B. Ali
(74) Attorney, Agent, or Firm—Ladas & Parry LLP

(57) ABSTRACT

The present invention provides an ankle-foot orthosis (1) that comprises a strut (2) extending over the front of the lower leg and anterior of the lateral ankle, a foot plate (3) extending beneath the sole of the foot and a fastening means for the fastening the orthosis (1) to the leg. The strut comprises a bifurcation zone (9) and two strut branches (2', 2") arranged to extend on the outside of the lower leg on each side of the tibia. Thus the present invention provides an orthosis (1) with high resistance against wear and tear, high wear comfort for the patient and an orthosis (1) enabling an almost normal gait.

11 Claims, 5 Drawing Sheets

ANKLE-FOOT ORTHOSIS

FIELD OF THE INVENTION

The present invention relates to an ankle-foot orthosis, particularly for patients suffering from so called drop foot, resulting from paralysis of the anterior muscles of the leg due to e.g. lesions of the peroneal nerve.

BACKGROUND OF THE INVENTION

U.S. Pat. No. 5,897,515 discloses an ankle-foot orthosis, comprising a frame of thin flexible material extending over the front of the lower leg, anterior of the lateral ankle and beneath the part of the sole of the foot and a supporting portion of rigid material extending over a narrow part of the front of the lower leg, anterior of the lateral ankle and beneath the part of the sole of the foot. The disclosed orthosis may be worn under the patients ordinary clothes and shoes.

U.S. Pat. No. 2,949,111 discloses a drop-foot brace comprising a supporting sole member to be placed into a shoe and beneath the foot of a handicapped person; a leg embracing member releasably applicable to the leg of said person: a bundle of closely adjacent flat springs and means for connecting the sole member to a lower end of the bundle and means for connecting an upper end of said bundle to the leg embracing member.

The orthoses disclosed in prior art usually refers to orthoses used by persons with severe drop foot or persons having severe muscle weakness in the lower extremities. These orthoses comprise a supporting portion of rigid material extending over a region between a strut on the lower leg and a foot plate. Due to the supporting portion these orthoses provide a strong support but may also be experienced as too rigid by some users, and further the supporting portion is sensitive to wear and tear during walking and may break, especially when used by heavy and very active persons.

There is a need for an improved ankle-foot orthosis to be used by persons having a milder drop foot or a lesser muscle weakness and thus do not need an orthosis as stiff as those disclosed by prior art. Since it is easier for these persons to walk than for persons having a severe drop foot, an improved ankle-foot orthosis with improved wear comfort is desired for these users. Such an ankle-foot orthosis is disclosed in the present invention.

SUMMARY OF THE INVENTION

It is an object of the present invention to provide an orthosis with an adequate stiffness, adjusted for people with milder drop foot, which preserves the supporting function. The object is achieved with an ankle-foot orthosis according to the present invention. The orthosis comprises a foot plate, arranged to extend beneath the sole of the foot. It further comprises a strut, arranged to extend from the lateral side of said foot plate over the front of the lower leg and anterior of the lateral ankle. The strut comprises a bifurcation that gives rise to two strut branches, arranged to extend on the lower leg. Also included are a fastening means for fastening the orthosis to the leg. Thus the present invention provides an orthosis with high resistance against wear and tear, high wear comfort for the patient and an orthosis enabling an almost normal gait.

BRIEF DESCRIPTION OF THE DRAWINGS

The present invention will be described in more detail with reference to the accompanying drawings, in which.

DETAILED DESCRIPTION OF THE PREFERRED EMBODIMENTS

Figure 1:
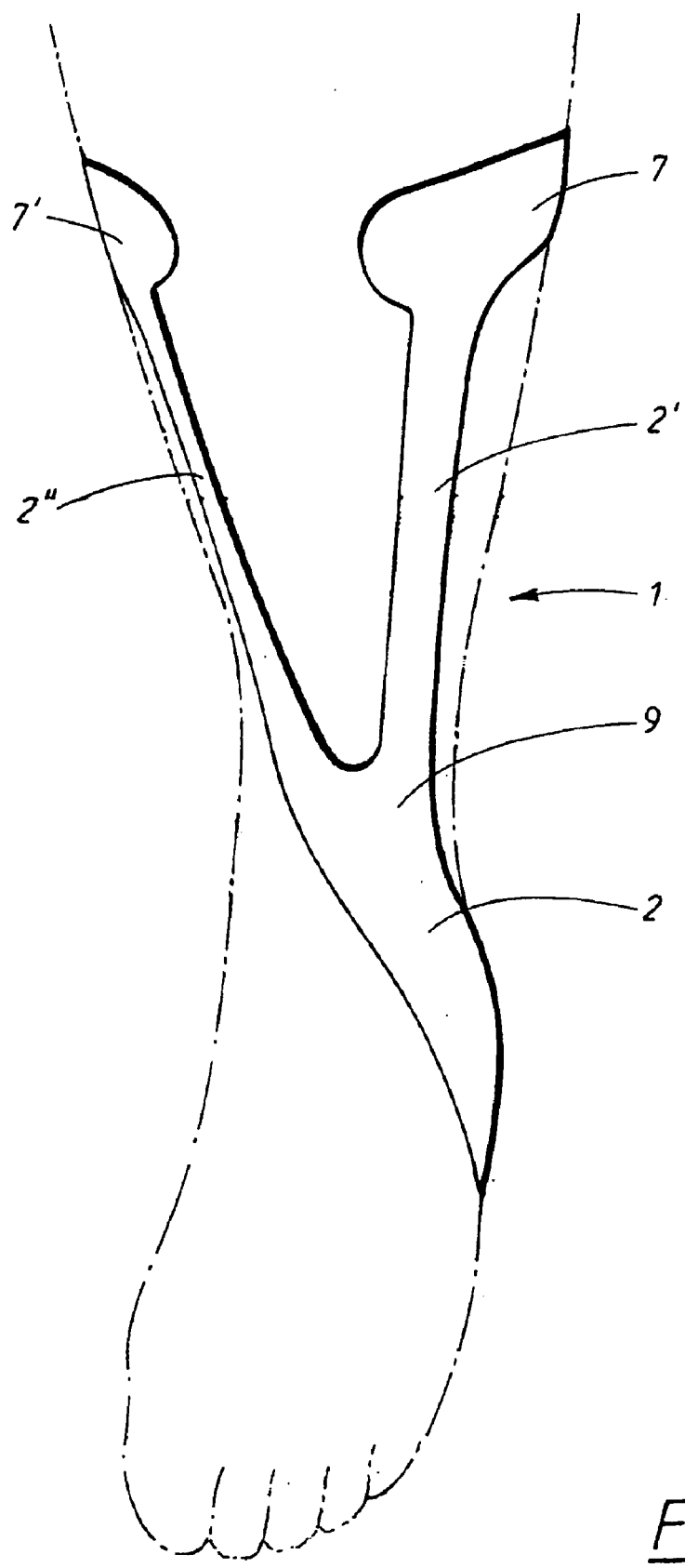
FIG. 1 shows an ankle-foot orthosis according to an embodiment of the present invention placed on the lower leg of a patient.
Figure 2:
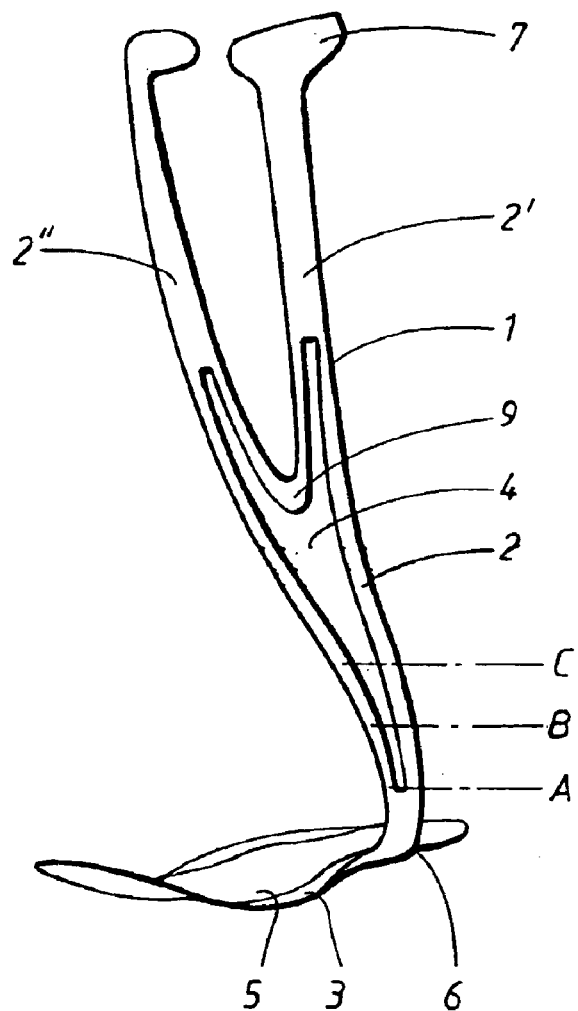
FIG. 2 shows a perspective view of the ankle-foot orthosis according to the invention.
Figure 3:
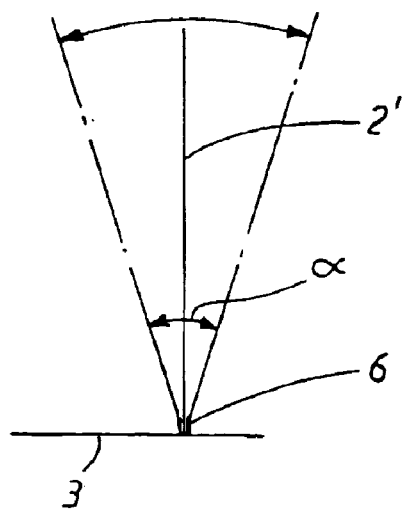
FIG. 3 shows the range of motion of the orthosis according to the present invention.

An ankle-foot orthosis according to the present invention is shown in FIG. 1 and FIG. 2. In the figures, an orthosis 1 for the left foot is shown while it should be understood that a mirror image of the orthosis should be used for the right foot.

Figure 6:
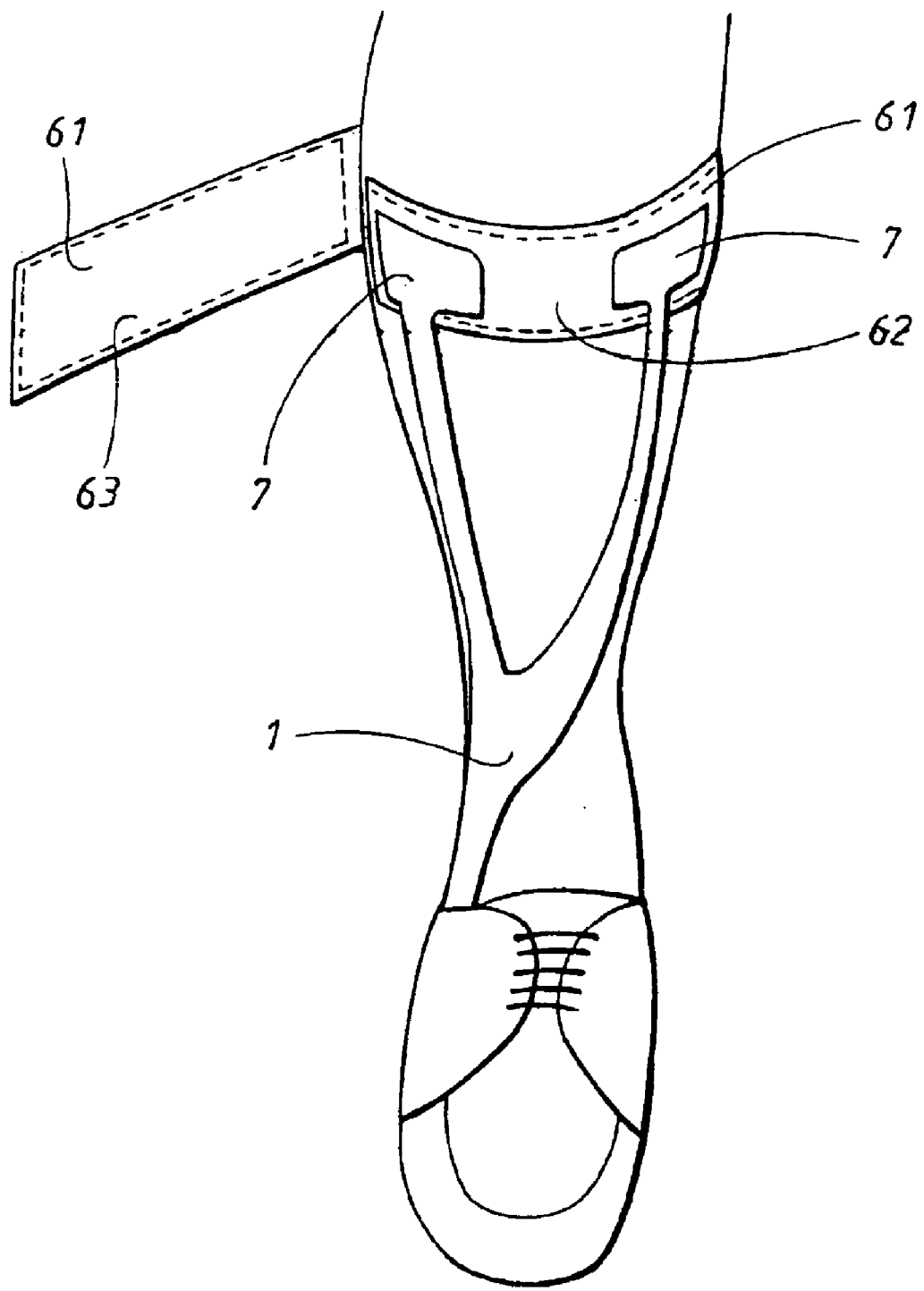
FIG. 6 shows an embodiment of the orthosis in the act of being strapped to a lower leg equipped with an ordinary shoe.

The ankle-foot orthosis 1 comprises a foot plate 3, arranged to be placed under the sole of a patients foot, and a fastening means (not shown), arranged in the upper portion of the orthosis 1 for fastening the orthosis 1 to the lower leg. The fastening means, preferably a strap, and the orthosis 1 are preferably provided with so-called VELCRO or "hook and loop" surfaces providing an easy means of taking on and off the orthosis 1. The strap 61 is preferably strapped on the lower leg having a hook type surface 62, on its first end 62, facing outwards, cf FIG. 6, in the area devised to be applied under the pads 7 of the ortosis 1. The orthosis 1 is then applied over said strap with a loop type surface on the pads 7 facing inwards to connect with the hook type surface 62. The orthosis is then secured further by strapping a second end 63 of the strap 61 having a loop type surface, over said pads 7 connecting with the hook type surface 62. A similar function can be achieved by having hook type surfaces instead of loop type surfaces, and vice versa.

The orthosis 1 further comprises a strut 2, arranged to extend from a lateral side of said foot plate anterior of the lateral ankle over the front of the lower leg. In the strut 2 a reinforcement element 4 is embedded. The reinforcement element 4 extends over a narrow part of the leg portion of the strut 2 on the front of the lower leg. The foot plate 3 also comprises another embedded element, viz. a tough flexible element 5. The tough element 5 is preferably made of aramid fiber (KEVLAR™). Kevlar is a little stiffer than cured glass fiber and a lot tougher. It does not break as easily as glass fiber. So the Kevlar element brings besides extra stiffness also a safety aspect. Thus the reinforcement element 4 and the tough flexible element 5 together provide the supporting portions of the orthosis 1.

The orthosis 1 is made of a light weight material and is preferably made from a yarn fabric of fiberglass, which is pre-impregnated with an epoxy matrix into a prepreg. Between the fiberglass layers, the two-part reinforcement element 4 is placed. Said reinforcement element can comprise carbon fibers.

The orthosis 1 does not comprise a special resilient member corresponding to the bundle of flat springs in U.S. Pat. No. 2,949,111. Because the strut 2 is not totally stiff, the strut branches 2', 2" and the foot plate 3 are movable relative each other, and when the angle between them is changed within the range (−α/2, α/2) from a rest position, the construction provides the orthosis 1 with an elastic range of motion due to elastic deformation in the strut branches/strut/foot plate connection. Thus the total elastic range of motion is α. The angle α varies depending on a number of factors.

Except where the reinforcement element 4 is embedded in the strut 2, the strut 2 is flexible. This means that the orthosis 1 can accommodate thick and thin legs by tightening or loosing the strap and moving the pads 7 on the strap. Also, the orthosis 1 may be cut by an ordinary pair of scissors to adjust width of the foot plate 3.

Figure 4:
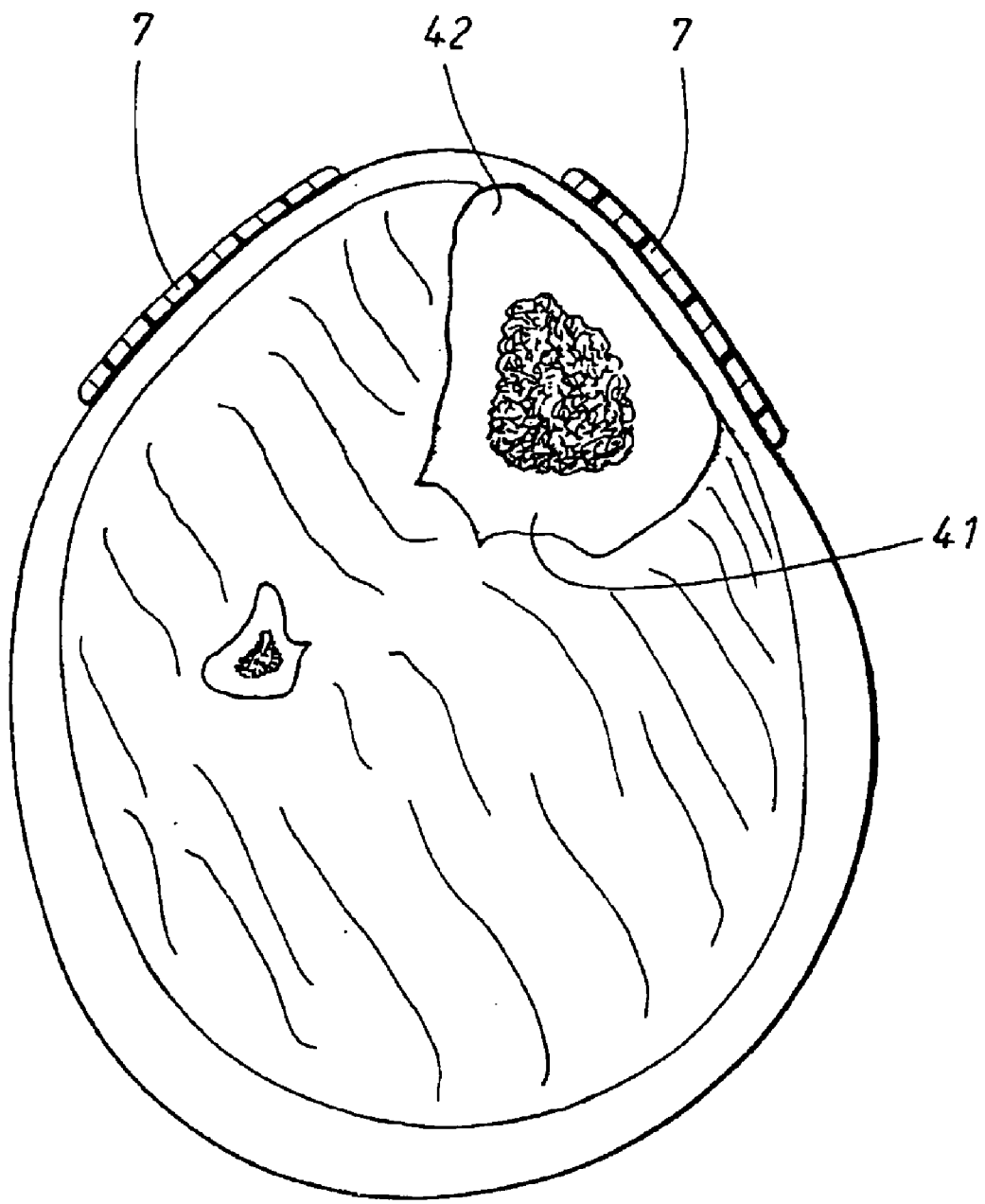
FIG. 4 shows a transverse section through the middle of left leg and orthosis as seen from above

In the orthosis 1 according to a preferred embodiment of the present invention, the strut 2 has two branches 2', 2" arranged to extend on each side of the tibia 41 of the patient, thus avoiding pressure on the tibia crest 42 as can be seen in FIG. 4. Further, each end of the branches 2', 2" comprises a horizontally arranged pad 7. The branches are made of a material that enables them to be twisted so that they are self-adjusting, i.e. positions of the pads 7 will adapt themselves to fit the curvature of the lower leg. Also the pads are made of a material that enables them to be somewhat flexible and self-adjusting. The pads 7 are preferably reinforced by carbon fiber. In one embodiment of the invention, one end of the fastening means, i.e. the strap, is arranged on the inside of one of the pads 7 using the VELCRO surfaces of the strap and the pad 7. In this embodiment the orthosis 1 is secured to the lower leg by wrapping the strap around the upper portion of the orthosis 1 and finally fastening the strap on the outside of the winding using the VELCRO surfaces on the inside and outside of the strap.

The orthosis 1 is preferably manufactured so that the finished product comprises a one-piece entity, i.e. there are no fastening devices like screws or rivets connecting the different parts, parts like the foot plate 3, the strut 2 and the strut branches 2', 2". This is accomplished by forming the orthosis of a composite fiber-reinforced material.

Figure 5:
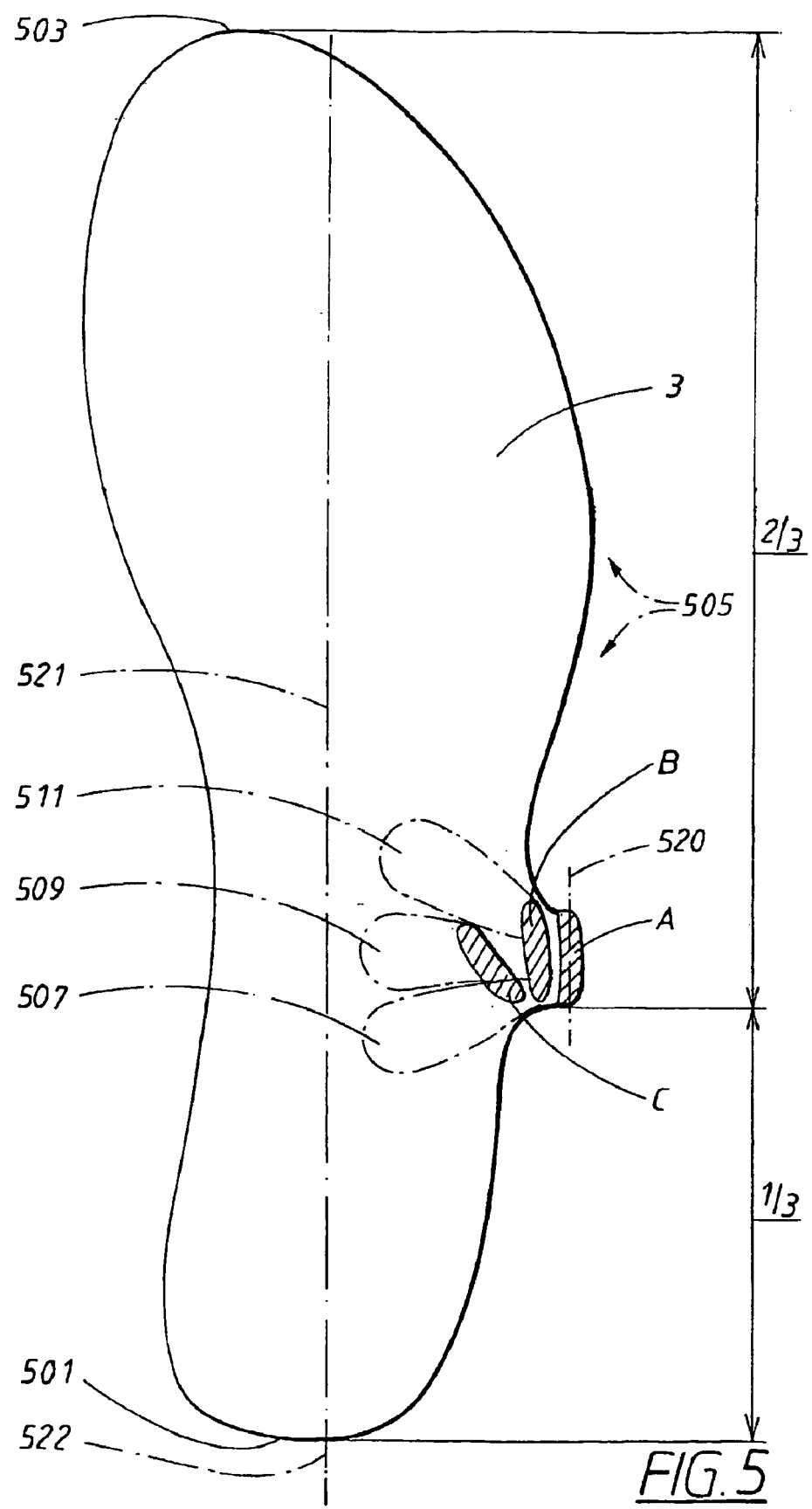
FIG. 5 shows a top view of a foot plate with cross sections at different heights.

FIG. 5 shows a foot plate of an orthosis intended for a right foot. The strut 2 emanates from a lateral side 55 of the foot plate 3. Approximately one third of the distance from a heel end 501 to a toe end 503 of the foot plate is arranged an anchor 507–511 comprising a number of fiberglass fabric layers 507–511 applied under the foot plate 3.

The strut 2 extends upwards orthogonally from the foot plate 2. The strut 2 is mainly rectangular in cross section at foot plate level. In FIG. 5 is shown cross sections at different distances form the foot plate, marked on FIG. 2, of the strut 2 showing their respective position and long axis angle relative to the foot plate. The rectangular cross section A has a long axis 520 parallel to a long axis 522 of the foot plate 3.

The first cross section A is parallel to the long axis 522 of the foot plate 3, a second cross section B, a bit above the foot plate, is somewhat tilted, and a third cross section C, even further above the foot plate, is twisted about 45 degrees counter-clockwise referring to the foot plate long axis 522.

Arranged in a position intended to land approximately one third up the lower leg is a strut bifurcation zone 9, in which the lower part of the strut 2 bifurcates into a strut lateral branch 2' and a strut medial branch 2". The bifurcation zone 9 is achieved by partly overlapping layers of prepreg. A "V" shape is preferred to divide the pressure comfortably at each side of the tibia crest. The lateral branch 2' is arranged to extend upwards on the lateral side of the lower leg and to end with a lateral pad 7. The medial branch 2" is arranged to extend from the bifurcation, to cross the front side of the lower leg, and to simultaneously extend upwards, over to the medial side of the lower leg, and to end with a medial pad 7.

The medial branch 2" is arranged with a cross section with higher flexural resistance, so that it, because of its greater length with reference to the lateral branch 2', comprises a flexural resistance that keeps the foot in a straight position without giving after more to one side or the other, when exposed to forces comparable to them being the result of the patient taking one step forward using the leg with the orthosis for pushing. In other words, the two branches (2',2") have equal flexural resistance at their pads (7).

The above mentioned difference in flexural resistance is accomplished by a thicker and wider cross section or by adding a reinforcement element to the medial branch 2".

The branches 2', 2" and pads 7', 7" can be reinforced by carbon fibre.

What is claimed is:

1. An ankle-foot orthosis (1) comprising:
   a foot plate (3) devised to be placed under a foot of a patient;
   a strut (2) connected to said foot plate (3) making it possible to fasten the orthosis to the lower leg; and
   fastening means (61,62,63) for fastening the orthosis (1), characterised in that the strut (2) extends from one side (505) of the foot plate (3) only and said strut (2) comprises a bifurcation zone (9) that gives rise to two branches (2',2") of the strut (2) arranged to extend on each side of the tibia.

2. An ankle-foot orthosis (1) according to claim 1, characterised in that the strut (2) extends from a lateral side (505) of the foot-plate (3) only.

3. An ankle-foot orthosis (1) according to claim 2, characterised in that said strut (2) extends from a small area being located approximately one third of the distance between a toe end (503) and a heel end (501) of said foot-plate (3) making it possible for the strut (2) to extend anterior relatively to the lateral ankle.

4. An ankle-foot orthosis (1) according to claim 3, characterised in that said bifurcation zone (9) is arranged approximately one third up the lower leg.

5. An ankle-foot orthosis (1) according to claim 4, characterised in that said bifurcation zone (9) is arranged having a "V" shape from which said two branches (2', 2") extend.

6. An ankle-foot orthosis (1) according to claim 1, characterised in that each top end of the branches (2',2") comprises a pad (7) devised to be arranged horizontally on the leg.

7. An ankle-foot orthosis (1) according to claim 6, characterised in that the branches (2',2") and pads (7) are made of a material that enables them to be twisted and to be self-adjusting.

8. An ankle-foot orthosis (1) according to claim 7, characterised in that the branches (2',2") and pads (7) are reinforced by carbon fiber.

9. An ankle-foot orthosis (1) according to claim 1, characterised in that the fastening means includes hook and loop surfaces.

10. An ankle-foot orthosis (1) according to claim 1, characterised in that the longer of the two branches (2',2") are arranged to have a cross section with higher flexural resistance than the shorter one, so that the two branches (2',2") have equal flexural resistance at their pads (7).

11. An ankle-foot orthosis (1) according to claim 1, where said orthosis (1) comprises a one-piece entity.

* * * * *